US009993456B2

(12) United States Patent
Compadre et al.

(10) Patent No.: US 9,993,456 B2
(45) Date of Patent: Jun. 12, 2018

(54) PREPARATION AND USE OF A COMPOSITION FOR PREVENTION AND MITIGATION OF THE EFFECTS OF RADIATION

(71) Applicants: BioVentures, LLC, Little Rock, AR (US); Universidad Tecnica Particular De Loja, Loja (EC); The United States of America as Represented by the Department of Veterans Affairs, Washington, DC (US)

(72) Inventors: Cesar M. Compadre, Little Rock, AR (US); Philip Breen, Little Rock, AR (US); Nukhet Aykin-Burns, Little Rock, AR (US); Martin Hauer-Jensen, Little Rock, AR (US); Raul G. Enriquez, Coyoacan (MX); Sujay Kharade, Little Rock, AR (US); Omar Malagon, Loja (EC); Yadira Ordonez, Loja (EC); Edgar Ojeda, Loja (EC); Shraddha Thakkar, Little Rock, AR (US); E. Nathalie Pineda, Little Rock, AR (US); Darin Jones, Little Rock, AR (US)

(73) Assignees: The Board of Trustees of the University of Arkansas, Little Rock, AR (US); Universidad Tecnica Particular De Loja, Loja (EC); The United States of America as Represented by the Department of Veterans Affairs, Washington, DC (US)

( * ) Notice: Subject to any disclaimer, the term of this patent is extended or adjusted under 35 U.S.C. 154(b) by 0 days. days.

(21) Appl. No.: 15/021,376

(22) PCT Filed: Sep. 15, 2014

(86) PCT No.: PCT/US2014/055657
§ 371 (c)(1),
(2) Date: Mar. 11, 2016

(87) PCT Pub. No.: WO2015/039029
PCT Pub. Date: Mar. 19, 2015

(65) Prior Publication Data
US 2016/0220530 A1 Aug. 4, 2016

Related U.S. Application Data

(60) Provisional application No. 61/877,655, filed on Sep. 13, 2013.

(51) Int. Cl.
A61K 31/35 (2006.01)
A61K 31/355 (2006.01)
A61K 36/185 (2006.01)

(52) U.S. Cl.
CPC .......... A61K 31/355 (2013.01); A61K 36/185 (2013.01); *A61K 2236/00* (2013.01); *A61K 2236/35* (2013.01); *A61K 2236/55* (2013.01)

(58) Field of Classification Search
USPC ......................................... 514/451; 424/727
See application file for complete search history.

(56) References Cited

U.S. PATENT DOCUMENTS

| 4,168,271 | A |   | 9/1979  | Cardenas et al.  |             |
|-----------|---|---|---------|------------------|-------------|
| 5,114,957 | A |   | 5/1992  | Hendler et al.   |             |
| 5,336,485 | A |   | 8/1994  | Fariss           |             |
| 5,591,772 | A |   | 1/1997  | Lane et al.      |             |
| 5,606,080 | A |   | 2/1997  | Ogata et al.     |             |
| 5,821,264 | A |   | 10/1998 | Lane et al.      |             |
| 5,827,878 | A |   | 10/1998 | Makishima et al. |             |
| 5,919,818 | A |   | 7/1999  | Lane et al.      |             |
| 5,929,057 | A |   | 7/1999  | Makishima et al. |             |
| 5,990,322 | A |   | 11/1999 | Lee et al.       |             |
| 6,133,312 | A |   | 10/2000 | Elson            |             |
| 6,143,770 | A |   | 11/2000 | Lane et al.      |             |
| 6,204,290 | B1|   | 3/2001  | Lane et al.      |             |
| 6,239,171 | B1|   | 5/2001  | Lane et al.      |             |
| 6,350,453 | B1|   | 2/2002  | Tan et al.       |             |
| 6,395,915 | B1| * | 5/2002  | Bellafiore ............ | C07D 311/72 549/413 |
| 6,410,752 | B1|   | 6/2002  | Kim et al.       |             |
| 6,417,223 | B1|   | 7/2002  | Sanders et al.   |             |
| 6,683,194 | B2|   | 1/2004  | Zhang et al.     |             |

(Continued)

FOREIGN PATENT DOCUMENTS

| WO | 1993009777 | 5/1993 |
|----|------------|--------|
| WO | 2000016772 | 3/2000 |

(Continued)

OTHER PUBLICATIONS

Swanson Health Product Delta-Fraction Tocotrienols, 2011.*
Berbee et al. CAS: 155:425170, 2011.*
Berbee, M. et al., "γ-Tocotrienol ameliorates intestinal radiation injury and reduces vascular oxidative stress after total-body irradiation by an HMG-CoA reductase-dependent mechanism," (2009) Radiation Research 171:596-605.
Buss, A.W. "Diastereoselective synthesis of alpha-tocopherol," Inauguraldissertation, Basel Nov. 11, 2008.

(Continued)

*Primary Examiner* — Rei Tsang Shiao
(74) *Attorney, Agent, or Firm* — Andrus Intellectual Property Law, LLP

(57) ABSTRACT

Plant extracts, compositions, pharmaceutical compositions and methods of making and using the same are provided herein. The compositions comprise γ-tocotrienol (GT3) and δ-tocotrienol (DT3) in ratios wherein the DT3 is predominate. The compositions are useful for radioprotection and radiomitigation in subjects in need thereof.

18 Claims, 12 Drawing Sheets

(56) References Cited

U.S. PATENT DOCUMENTS

| | | | |
|---|---|---|---|
| 6,716,873 | B1 | 4/2004 | Keramidas et al. |
| 6,770,672 | B1 | 8/2004 | Sanders et al. |
| 7,105,686 | B2 | 9/2006 | Giraudi et al. |
| 7,642,064 | B2 | 1/2010 | Bieniarz et al. |
| 7,799,782 | B2 * | 9/2010 | Munson ............... C07D 231/56 514/234.5 |
| 8,044,161 | B2 | 10/2011 | Tiitinen et al. |
| 9,309,547 | B2 | 4/2016 | Zheng |
| 2005/0037102 | A1 | 2/2005 | Tan et al. |
| 2009/0036354 | A1 | 2/2009 | Gavin et al. |
| 2009/0041870 | A1 * | 2/2009 | Tan ....................... A61K 31/355 424/727 |
| 2010/0003716 | A1 | 1/2010 | Cervin et al. |
| 2010/0036079 | A1 | 2/2010 | Tiitinen et al. |
| 2011/0293753 | A1 * | 12/2011 | Bellafiore ............ A61K 9/4875 424/727 |
| 2015/0087033 | A1 | 3/2015 | Zheng |
| 2015/0158106 | A1 | 6/2015 | Peters et al. |

FOREIGN PATENT DOCUMENTS

| | | | |
|---|---|---|---|
| WO | 2001058889 | | 8/2001 |
| WO | 2003039461 | | 5/2003 |
| WO | WO2005/009135 | * | 2/2005 |
| WO | 2011001258 | | 1/2011 |
| WO | 2011150312 | | 12/2011 |
| WO | 2011153353 | | 12/2011 |
| WO | 2013176745 | | 11/2013 |
| WO | 2015039029 | | 3/2015 |

OTHER PUBLICATIONS

Ghosh, S.P. et al., "Chemistry of tocotrienols," (2009) Tocotrienols: Vitamin E beyond tocopherols, CRC Press, Edited by Ronald Ross Watson and Victor R. Preedy, 7:85-96.

Ghosh, S.P. et al., "Gamma-tocotrienol, a tocol antioxidant as a potent radioprotector," (2009) Int. J. Radiat. Biol. 85 (7):598-606.

Ko, S. N. et al., "The Concentration of Tocols from Rice Brain Oil Deodorizer Distillate Using Solvent," (2008) Eur. J. Technol. 110:914-919.

Krager, K. et al., "Tocotrienol-Rich Fraction from Rice Bran Demonstrates Potent Radiation Protection Activity," (2015) Evidence-Based Complementary and Alternative Medicine, 1-9.

Kumar, K. S. et al., "Gamma-tocotrienol: Potential as a countermeasure against radiological threat," (2009) Tocotrienols: Vitamin E beyond tocopherols, CRC Press, Edited by Ronald Ross Watson and Victor R. Preedy, 27:379-398.

Leth, T. et al., "Biological activity of Vitamin E compounds and natural materials by the resorption-gestation test, and chemical determination of the Vitamin E activity in foods and feeds," (1977) J. Nutr. 107:2236-2243.

Odinokov, et al. (ARKIVOC, 200 (xiii) 101-118).

Panagabko, C. et al., "Ligand specificity in the CRAL-TRIO protein family," (2003) Biochem 42:6467-6474.

Puah, et al., "The effect of physical refining on palm vitamin E," tocopherol, tocotrienol and tocomonoenol, American Journal of Applied Sciences (2007) 4(6):374-377.

Rammell, et al., "Separation of tocols by HPLC on an amino-cyano polar phase column," J. of Liquid Chromatography (1985) 8(4):707-717.

International Search Report and Written Opinion for International Application No. PCT/US2011/038933 dated Sep. 12, 2011 (11 pages).

International Search Report and Written Opinion for International Application No. PCT/US2013/030862 dated May 28, 2013 (20 pages).

Office Action for U.S. Appl. No. 13/701,630 dated Mar. 10, 2014 (19 pages).

International Search Report and Written Opinion for International Application No. PCT/US2014/055657 dated Dec. 22, 2014 (10 pages).

Office Action for U.S. Appl. No. 13/701,630 dated Dec. 31, 2014 (23 pages).

Office Action for U.S. Appl. No. 14/402,792 dated Aug. 5, 2015 (11 pages).

Office Action for U.S. Appl. No. 13/701,630 dated Aug. 12, 2015 (27 pages).

Office Action for U.S. Appl. No. 13/701,630 dated Jun. 1, 2016 (25 pages).

Singh, V.K., et al. Vitamin E: tocopherols and tocotrienols as potential radiation countermeasures, Journal of Radiation Research, 2013, pp. 973-988, vol. 54.

Krager, Kimberly J et al, "Tocotrienol-Rich Fraction from Rice Bran Demonstrates Potent Radiation Protection Activity" Evidence-Based Complementary and Alternative Medicine, 2015, vol. 2015, Article ID 148791,9 pages.

Ross, Caitlin et al, "Oxygen tension changes the rate of migration of human skin keratinocytes in an age-related manner" Exp Dermatol., Jan. 2011, 20(1): 58-63.

Uchida, Tomono, et al., "Tissue Distribution of alpha- and gamma-Tocotrienol and gamma-Tocopherol in Rats and Interference with Their Accumulation by alpha-Tocopherol" Lipids, 2012, 47:129-139.

* cited by examiner

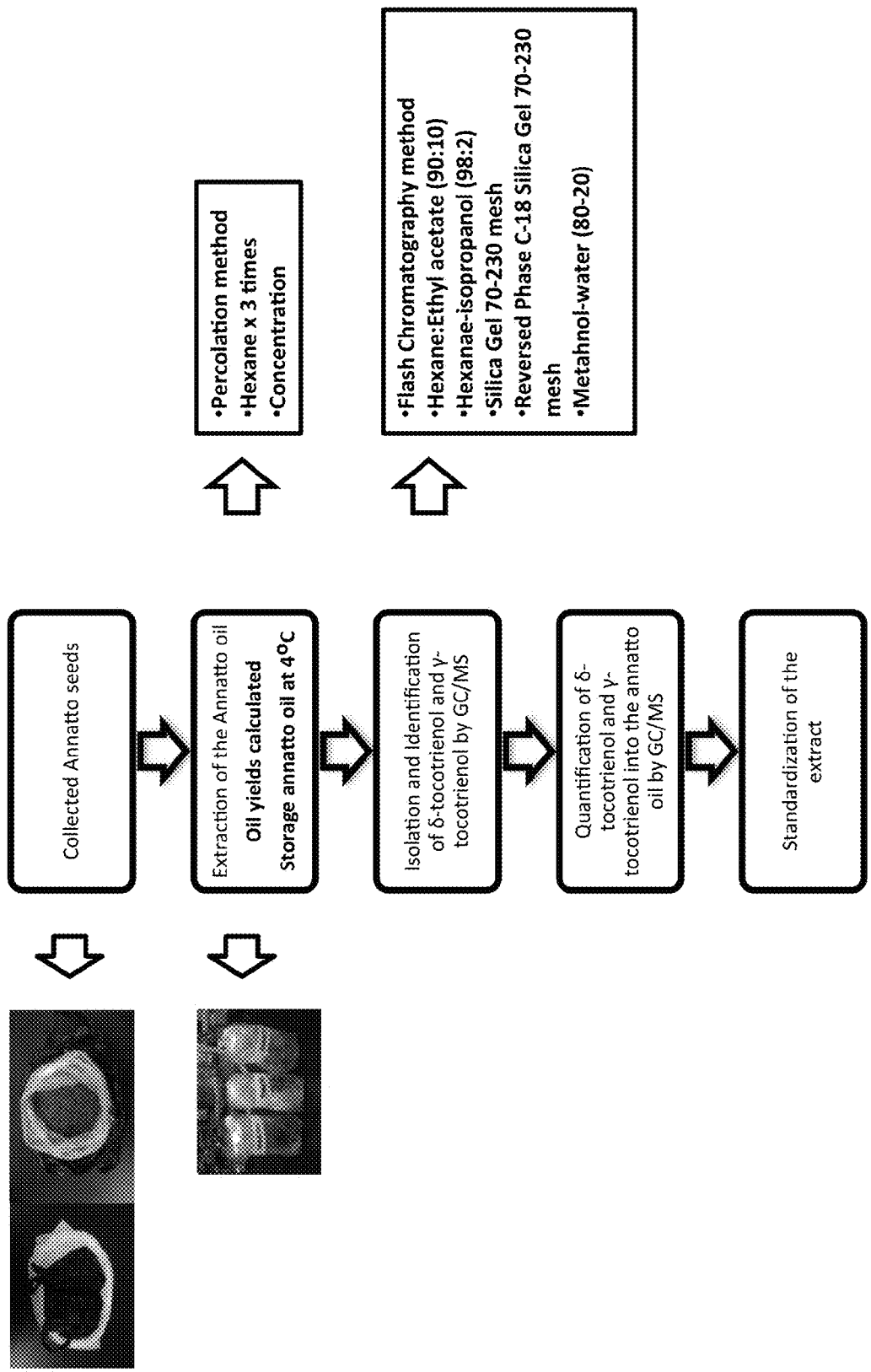

PREPARATION AND USE OF A COMPOSITION FOR PREVENTION AND MITIGATION OF THE EFFECTS OF RADIATION

CROSS-REFERENCE TO RELATED APPLICATIONS

This patent application is a national stage filing under 35 U.S.C. 371 of International Application No. PCT/US2014/055657, filed Sep. 15, 2014, which claims the benefit of priority of U.S. Provisional Patent Application No. 61/877,655, filed Sep. 13, 2013, both of which are incorporated herein by reference in their entireties.

STATEMENT REGARDING FEDERALLY-SPONSORED RESEARCH

This invention was made with United States government support awarded by the National Institutes of Health, grant number UL1 RR029884. The United States has certain rights in this invention.

BACKGROUND AND FIELD OF INVENTION

Vitamin E is composed of eight naturally occurring tocols. Four are tocopherols, which possess a saturated hydrocarbon tail, and four are tocotrienols, which possess three trans double bonds in the hydrocarbon tail. The tocols are known to have beneficial health effects when provided as a dietary supplement. The tocotrienols have recently been shown to have beneficial health effects not seen with the tocopherols.

Commercially available tocotrienols are purified from natural oils, where they occur as complex mixtures of tocotrienols and tocopherols. It is very difficult to separate the pure tocotrienols from these mixtures and therefore these compounds are very expensive. It is also difficult to obtain the tocotrienols in concentrations high enough for use in some applications.

This invention relates to the preparation of a composition containing tocotrienols and other compounds, the compositions produced by the method and the use of the compositions in a dose effective to prevent and mitigate the effects of radiation.

SUMMARY

Provided herein is a method of preparing a composition having tocotrienols and low or absent tocopherols. Further, a method of purification, enrichment, and standardization is described which results in a dose that shows effective radioprotective activity without toxicity. Also provided are the compositions and methods of using the compositions which show synergism over and above the effect shown by the individual tocotrienol constituents. The composition has a combination of δ-tocotrienol and γ-tocotrienol in a ratio from 2:1 to 10:1. First, the oil is extracted from tocotrienol containing plants such as annatto, rice, palm or wheat. Then, the tocotrienols are separated from the extract via chromatography. Compositions made by the methods are also provided.

In another aspect, a composition comprising δ-tocotrienol and γ-tocotrienol in a ratio of between 2:1 and 10:1 is provided. Suitably the composition has a ratio of between 5:1 and 9:1. Suitably the extract has a ratio of between 7:1 and 9:1. The compositions suitably have higher concentrations of δ-tocotrienol than γ-tocotrienol. The compositions have a total tocotrienol content between 15% and 95%. Suitably at least 30%, 40%, 45%, 50%, 55%, 60%, 70%, 80%, 90% or 95% of the composition is tocotrienols. The compositions include over 100 mg/mL, 200 mg/mL, 300 mg/mL, 400 mg/mL, 500 mg/mL, 600 mg/mL, 700 mg/mL, 800 mg/mL, 900 mg/mL or 1 g/mL total tocotrienols.

In still another aspect, methods of treating a subject with a condition or disease are provided. The methods include administering an effective amount of at least one of the described compositions to the subject to ameliorate the condition or disease. The subject may be in need of treatment with a radioprotectant or for treatment of radiation exposure or an antioxidant, an anti-inflammatory agent, an immunoregulatory agent, an anti-thrombotic agent, an anti-atherogenic agent, a hypocholesterolemic agent or an HMG-CoA reductase inhibitor. The subject may have a condition or disease selected from radiation exposure, cancer, cardiovascular disease including but not limited to coronary artery disease, elevated lipoprotein levels, elevated cholesterol levels, elevated triglycerides, age-related macular degeneration, cataracts, glaucoma, chronic pain, chronic fatigue syndrome, fever, edema, diabetes mellitus, signs of aging, rheumatoid diseases, septic shock, and Alzheimer's disease.

BRIEF DESCRIPTION OF THE DRAWINGS

FIG. 1 shows the extraction procedure for producing the annatto extract comprising δ-tocotrienol and γ-tocotrienol called DG-3

FIG. 2 shows the mass spectroscopy profiles of the annatto extract, DG-3.

DETAILED DESCRIPTION

Figure 2B:
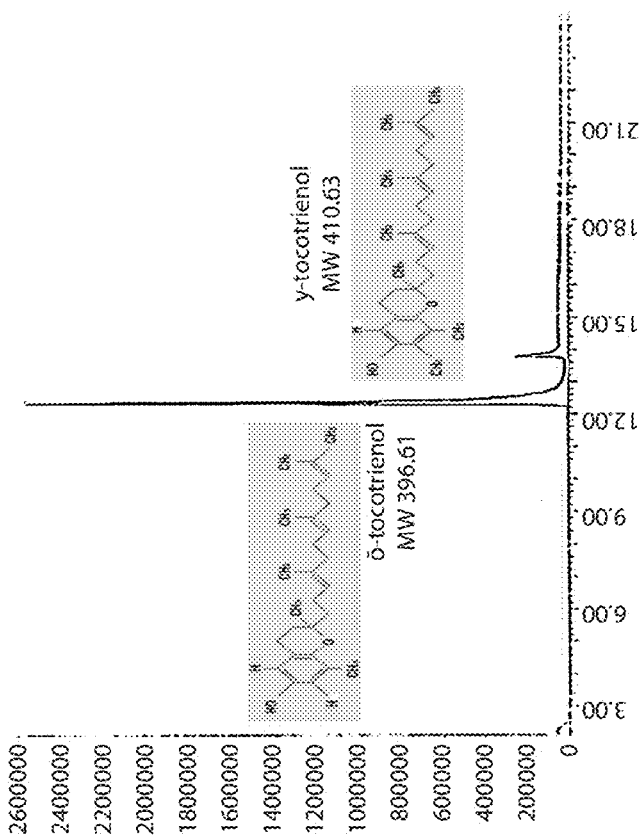
FIG. 2A shows the crude extract and FIG. 2B shows the standardized extract.

Radiation therapy used in the definitive management and palliative care of cancer patients frequently results in acute and late radiation-induced normal tissue toxicity. Radiation exposure through inadvertent release of nuclear material, such as the Fukishima reactor, is additionally problematic and few treatment options are available. Therefore there is an imminent need for safe and effective radioprotectors to improve the quality of life in patients who receive radiotherapy or are exposed to radiation.

Among the naturally occurring vitamin E analogs, γ-tocotrienol (GT3) and δ-tocotrienol (DT3) are the two members, which have shown significant radioprotectant and radiomitigator abilities. Studies suggested numerous mechanisms by which GT3 and DT3 exert their radioprotective effects, including enhancing eNOS activity via regulation of tetrahydrobiopterin availability and preventing DNA damage to hematopoietic stem and progenitor cells via stimulation of MTOR survival pathways. Unfortunately both DT3 and GT3 are difficult to purify and very expensive, and most tocotrienol rich oils available contain very substantial amounts of tocopherols, that may interfere with the bioavailability and bioactivity of the tocotrienols.

DG-3, provided herein, is a standardized extract derived from annatto seeds that contains only DT13 and GT3. Because radiation-induced mitochondrial damage and oxidative stress impacts several critical biologic parameters such as DNA damage repair and stem cell fate, in this research we have compared the effects of DT3, GT3, and DG-3 against radiation induced mitochondrial dysfunction and oxidative stress. Our initial results indicate that treatment with 5 µM DT3 or DG-3 did not change the H9C2 rat heart cardiomyocyte cells' total antioxidant capacity (measured as copper reducing equivalents). Furthermore, the same treatment preserved the cell viability and mitochondrial respiration in these cells when followed by oxidative insult via $H_2O_2$ treatment. Methods of making DG-3 and methods of using these compositions are provided herein.

The annatto seed extract, called DG-3, provided herein was made by the method depicted in FIG. 1. The method begins by collecting annatto seeds and extracting the oil from the annatto seeds to produce an annatto seed oil. Notably, rice, palm and wheat may also serve as the source of the tocotrienol compositions provided herein. The oil may be extracted using hot or cold solvent extraction, such as hexane extraction as described in the examples. Other methods of extracting oil from an oilseed such as a cold or hot press via extruders or presses may also be utilized. The annatto seeds may be prepared for these processes using standard methods known to those of skill in the art. The annatto oil is suitably stored at 4° C. until used and may be concentrated via methods described in the examples or via condensation or dehydration methods know to those of skill in the art.

The preparation of the tocotrienol composition includes further enrichment and purification using chromatographic techniques using normal or reverse stationary phases and mixtures of solvents such as acetone, ethylene dichloride, hexane, isopropyl alcohol, propyl alcohol, methyl-alcohol, methylene chloride, trichloroethylene, and water. In the Examples, flash chromatography using a hexane:ethyl acetate solvent (90:10) followed by a second separation using a hexane:isopropanol (98:2) solvent and silica gels (70-230 mesh) was used. Those of skill in the art will appreciate that the precise chromatography methods can be altered to obtain separated tocotrienol compositions.

Figure 2A:
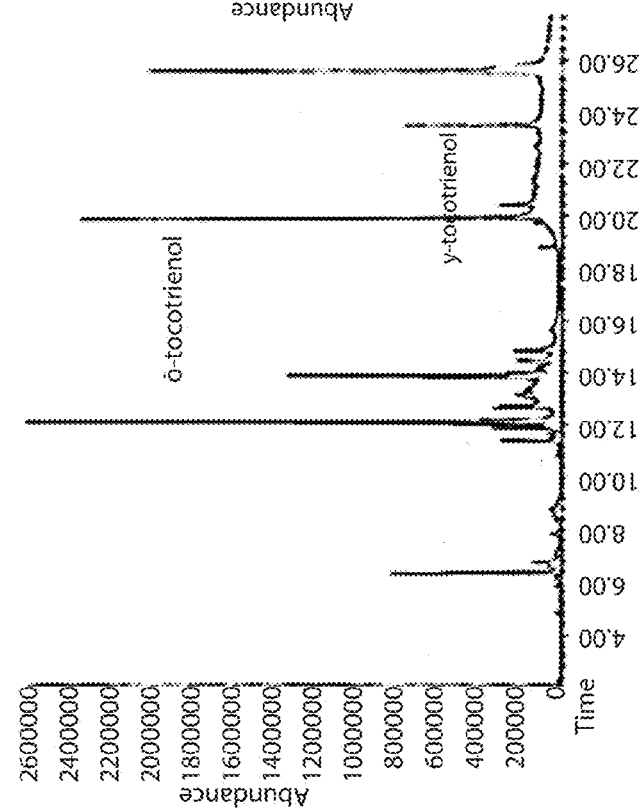

The annatto seed extract compositions were then analyzed by gas chromatography mass spectroscopy to produce the graphs of FIG. 2. As shown in FIG. 2B, the DG-3 standardized extract provided herein contains few contaminants, such as tocopherols, and is rich in δ-tocotrienol and γ-tocotrienol. Finally, the extract compositions were standardized by mixing two extracts of known concentrations in the proper proportions to achieve the extract with the target composition (a 7:1 ratio of δ-tocotrienol to γ-tocotrienol). For the standardization one extract has a concentration above target and the other below target. Production of an extract having a standardized composition is very important from the pharmaceutical point because content uniformity is necessary for accurate dosing.

The DG-3 annatto seed extract provided herein has a ratio of about 7:1 δ-tocotrienol to γ-tocotrienol. The DG-3 annatto seed extract compositions may have a δ-tocotrienol to γ-tocotrienol of between 2:1 to 10:1, suitably between 5:1 to 9:1 and suitably between 7:1 and 9:1. Delta tocotrienol is the predominate component. The compositions have a total tocotrienol content between 15% and 95%. Suitably at least 30%, 40%, 45%, 50%, 55%, 60%, 70%, 80%, 90% or 95% of the composition is tocotrienols. Suitably, the compositions have less than 5% tocopherols, suitably less than 2%, less that 1%, less than 0.1%, or even no detectable tocopherols. The compositions may be substantially free of tocopherols. The tocopherols may decrease the effectiveness of the tocotrienols in the methods of treatment described herein.

Pharmaceutical compositions comprising the DG-3 annatto seed extracts described herein are also provided. Suitably the compositions contain 100 µM, 200 µM, 250 µM, 300 µM, 400 µM, 500 µM, 1 mM, 2 mM, 3 mM, 4 mM, 5 mM, 10 mM, 25 mM, 50 mM, 100 mM, 200 mM, 250 mM, 300 mM, 400 mM, 500 mM or 1 M total tocotrienols. Suitably the pharmaceutical compositions contain 10 mg/mL, 25 mg/mL, 50 mg/mL, 75 mg/mL, 100 mg/mL, 200 mg/mL, 250 mg/mL, 300 mg/mL, 400 mg/mL, 500 mg/mL, 600 mg/mL, 700 mg/mL, 800 mg/mL, 900 mg/mL or g/mL total tocotrienols. A single dosage form may contain 200 mg, 300 mg, 400 mg, 500 mg, 600 mg, 700 mg, 800 mg, 900 mg, 1 g, 2 g, 5 g, or 10 g per dose. The Examples in mice showed efficacy for a single 300 mg/Kg dose to protect from a lethal dose of radiation. Efficacy to treat radiation effects, such as those in radiotherapy for cancer, would likely require lower doses. However, multiple, divided doses will cause blood levels to accumulate over time. Thus lower doses may also be useful if provided in more than a single dose. Moreover, the beneficial biochemical changes induced by the tocotrienols are likely to be cumulative.

The compositions described herein may be used in methods of treating subjects. The compositions may be used to treat subjects in need of a radioprotectant, radiomitigator or for treatment of radiation exposure. In addition, the compositions may be used to treat subjects in need of treatment with an antioxidant agent, an anti-inflammatory agent, an immunoregulatory agent, an anti-thrombotic agent, an anti-atherogenic agent, a hypocholesterolemic agent or an HMG-CoA reductase inhibitor. The methods of treatment are based on administering an effective amount of the compositions provided herein to subjects in need of such treatment.

The compositions may be used to make pharmaceutical compositions. Pharmaceutical compositions comprising the compositions described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based solutions or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified. In the Examples, a pharmaceutical composition comprising the tocotrienols, Tween 80 and Polyethylene glycol 80 was used.

The compositions described herein may be used to treat a subject with a condition selected from radiation exposure, cancer, cardiovascular disease including but not limited to coronary artery disease, elevated lipoprotein levels, elevated cholesterol levels, elevated triglyceride levels, atherosclerosis, ischemia-reperfusion injury and the like, age-related macular degeneration, cataracts, glaucoma, chronic pain, chronic fatigue syndrome, fever, edema, diabetes mellitus, signs of aging, rheumatoid diseases, septic shock, inflammatory diseases, autoimmune diseases or Alzheimer's disease. In the case of radiation exposure, the compositions may be delivered as a radioprotective agent to a subject prior to potential exposure to radiation, such as to a patient receiving radiation therapy, or a person working with or cleaning up radiation or a radiation spill or leak. The compositions may also be given after radiation exposure as a radiomitigator, such as after an accident involving the release of radiation.

Treatment of a condition includes but is not limited to, prophylaxis of symptoms or indicators of the condition, reduction in disease severity, or reversal, reduction or slowing in disease progression as compared to an untreated subject. The compositions described herein may be used to treat subjects in need of treatment with a radioprotectant, an antioxidant, an anti-inflammatory, immunoregulatory, anti-thrombotic, antiatherogenic, hypocholesterolemic or an HMG-CoA reductase inhibitor. Combination therapy with a known antioxidant, anti-inflammatory or HMG-CoA reductase inhibitor may result in increased effectiveness of the combination treatment as compared to treatment with either composition alone.

The compositions described herein may be administered by any means known to those skilled in the art, including, but not limited to, oral, topical, intranasal, intraperitoneal, parenteral, intravenous, intramuscular, or subcutaneous. In the Examples, a subcutaneous injection was used. Thus the compositions may be formulated as an ingestible, injectable, topical or suppository formulation. The compositions may also be delivered within a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects as compared to administration of a smaller amount. Moreover, efficacy is also contemplated at dosages below the level at which toxicity is seen.

It will be appreciated that the specific dosage administered in any given case will be adjusted in accordance with the compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the composition of the invention and of a known agent such as tocopherol, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will reduce symptoms of the condition at least 10%, 20%, 30%, 40%, 50%, 60%, 70%, 80%, 90% or 100% compared to pre-treatment symptoms or symptoms if left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 1,000 milligrams per kilogram of body weight, although they are typically about 500 milligrams or less per kilogram of body weight. Like other vitamin E compounds, large doses may be required for therapeutic effect and toxicity is likely low. In some embodiments, the effective dosage amount ranges from about 10 to about 1,000 milligrams per kilogram of body weight in a single dose or provided daily or weekly. In another embodiment, the effective dosage amount ranges from about 50 to about 500 milligrams per kilogram of body weight in a single dose or provided daily or weekly. In another embodiment, the effective dosage amount ranges from about 75 to about 300 milligrams per kilogram of body weight in a single dose or provided daily or weekly. In the Examples, a single dose of 300 mg/Kg was found to protect mice from a subsequent lethal or sub-lethal exposure to radiation. The effective dosage amounts described herein refer to total amounts administered, that is, if more than one composition is administered the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Preparation and Analysis of DG-3 Annatto Extract

Triturated annatto seeds, 200 g, were extracted with 400 mL of hexane for 24 h. The extract was filtered under vacuum and the resulting liquid was concentrated under reduced pressure. The residue was further extracted with 400 mL of hexane, repeating this process for a total of 3 times. Each of the extracts was dissolved in 10 mL of hexane. 1 ml of the solution for each sample was used for analysis by GC/MS.

Alternatively, 200 g of annatto seeds were weighed and put into water for 3 days in order to remove the seeds' coloring. The water was discarded and the seeds were removed and crushed, then added to 400 mL of hexane for 24 h, followed by filtration under vacuum. The resulting liquid was concentrated under reduced pressure. The residue was again extracted with 400 mL of hexane, repeating this process for a total of 3 times.

The tocotrienol content of the extracts was further enriched by elution through a chromatography system in which the stationary phase was silica gel (70-230 mesh, grade 60), and the mobile phase was a mixture of hexane: ethyl acetate (90:10). The extract was further enriched and purified by an additional chromatography step using hexane: isopropanol (98:2). In addition to an enrichment in tocotrienols, these chromatography steps are used to remove undesirable phytochemicals such as the sterols.

GC/MS

The measurements were performed by injecting 2 μL of sample into a GC/MS (Agilent 5975 GC/MSD) for quantitation. The GC was equipped with a 30 m HP-5 MS column (0.250 mm 10 μm, Agilent). Helium was used as carrier gas with a head pressure of 27.64 psi, splitless, with a purge flow of 50 mL/min after 1 min. Injector and transfer line were maintained at 275° C. and 285° C. respectively. Column temperature was maintained at 220° C. for 2 min followed by a gradient of 10 C/min to 285° C., maintained at his temperature for 5 min, followed by final gradient of 25 C/min to 300° C. and maintained at this temperature for 10 min. The mass spectrometer conditions were electron impact, ion source temperature 230° C., MS quadrupole 150° C., and ionization voltage 70 eV for single ion mode. See FIG. 2.

Calibration and Linearity

A five-point calibration curve for analyses was obtained by plotting the peak-area vs. the concentration of DT3 standard. The following concentrations were used for the calibration curve: $2.0 \times 10^{-5}$, $8.0 \times 10^{-5}$, $18.0 \times 10^{-5}$, $27.0 \times 10^{-5}$, and $38.0 \times 10^{-5}$ mg/mL. Linearity was established over this concentration range: y=74081x−92908, where x is the concentration of δ-tocotrienol and y is the peak-area. The goodness of fit ($r^2$) was 0.999. The coefficient of variation (CV) for the lowest concentration, $0.56 \times 10^{-10}$ μg/μL, was 16.97%, which is less than the maximum acceptable value of 20% for the LOQ [2].

For δ-tocotrienol, a five-point calibration curve for analyses was obtained by plotting the peak-area ratio of δ-tocotrienol to α-tocotrienol versus known δ-tocotrienol concentration. 32 ng of α-tocotrienol was added to every sample as an internal standard. Concentrations of $0.04 \times 10^{-10}$, $0.15 \times 10^{-10}$, $0.58 \times 10^{-10}$, $2.25 \times 10^{-10}$, and $9.00 \times 10^{10}$ μg/L were used for the calibration curve. Linearity was established over the concentration range: $y=1.788x+0.280$, where x is the concentration of δ-tocotrienol and y is the peak-area ratio. The goodness of fit ($r^2$) is 0.999. The coefficient of variation (CV) for the lowest concentration, $2.0\times10-5$ mg/mL, was 12%, which is less than the maximum acceptable value of 20% for the LOQ [2].

The coefficients of variation for all the other concentrations were less than the maximum 15% allowed.

Table 1 below shows the results of the two extraction procedures:

| Analysis | Samples | area | Conc. mg/mL × 10E−5 | mg DT3/mg mg × 10E−3 | | % |
|---|---|---|---|---|---|---|
| first analysis | Sample_1 | 1093430 | 16.01 | 1.60 | 0.00160 | 1.60E−01 |
| | Sample_2 | 1608422 | 22.97 | 2.30 | 0.00230 | 2.30E−01 |
| | Sample_3 | 1486154 | 21.32 | 2.13 | 0.00213 | 2.13E−01 |
| second analysis | Sample_4 | 474901 | 7.66 | 0.77 | 0.00077 | 7.70E−02 |
| | Sample_5 | 268490 | 4.89 | 0.49 | 0.00049 | 4.90E−02 |
| | Sample_6 | 279986 | 5.03 | 0.50 | 0.00050 | 5.00E−02 |
| | Chuno | 931534 | 13.83 | 1.38 | 0.00138 | 1.38E−01 |

Morphology Assay

Figure 3:
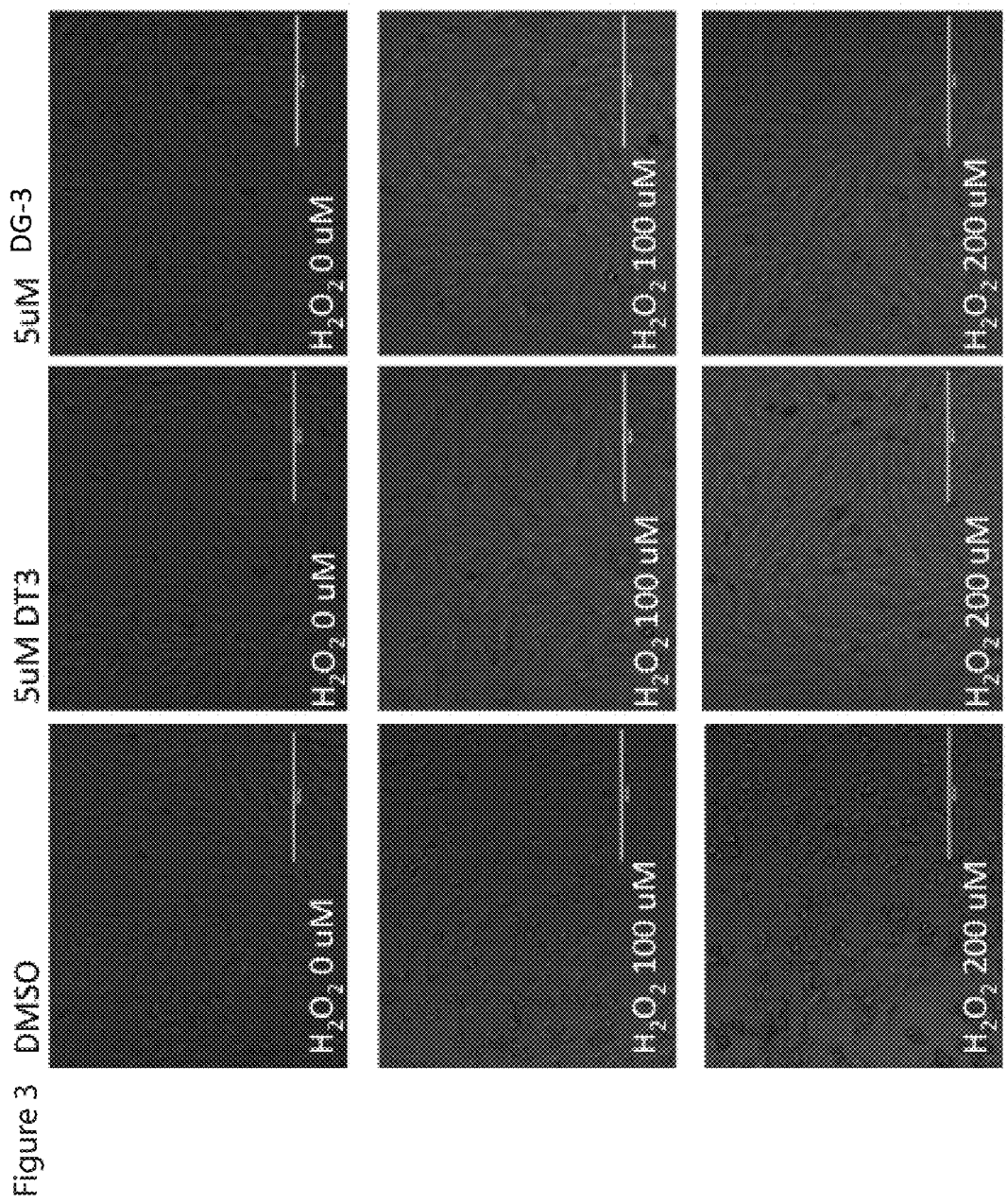
FIG. 3 is a set of photographs showing the cardiomyocytes after the indicated treatments. H9C2 heart cardiomyocytes were treated with 5 μM DT3 or 5 μM DG-3 or vehicle control (DMSO) overnight. Cells were then exposed to $H_2O_2$ for 4 h. Morphological changes were recorded under an inverted microscope.

H9c2 heart cardiomyocytes were treated with 5 μM DT3 or 5 μM DG-3 or vehicle control (DMSO) overnight. Cells were then exposed to 100 or 200 μM $H_2O_2$ for 4 h. Morphological changes were recorded under an inverted microscope. As shown in FIG. 3, the cells not treated with $H_2O_2$ appear as a confluent monolayer of healthy cells. The cells treated with 100 μM $H_2O_2$ show some damage after 4 hours, but the damage is limited by treatment with either DT3 or DG-3 as shown by rounded cells and breaks in the cell monolayer. After treatment with 200 μM $1H_2O_2$, the untreated cells show a large number of rounded and dying cells, while the DT3 and DG-3 treated cells still maintain a monolayer with only a few rounded cells.

Ability of the DG-3 to Inhibit Lipid Peroxidation

Figure 4:
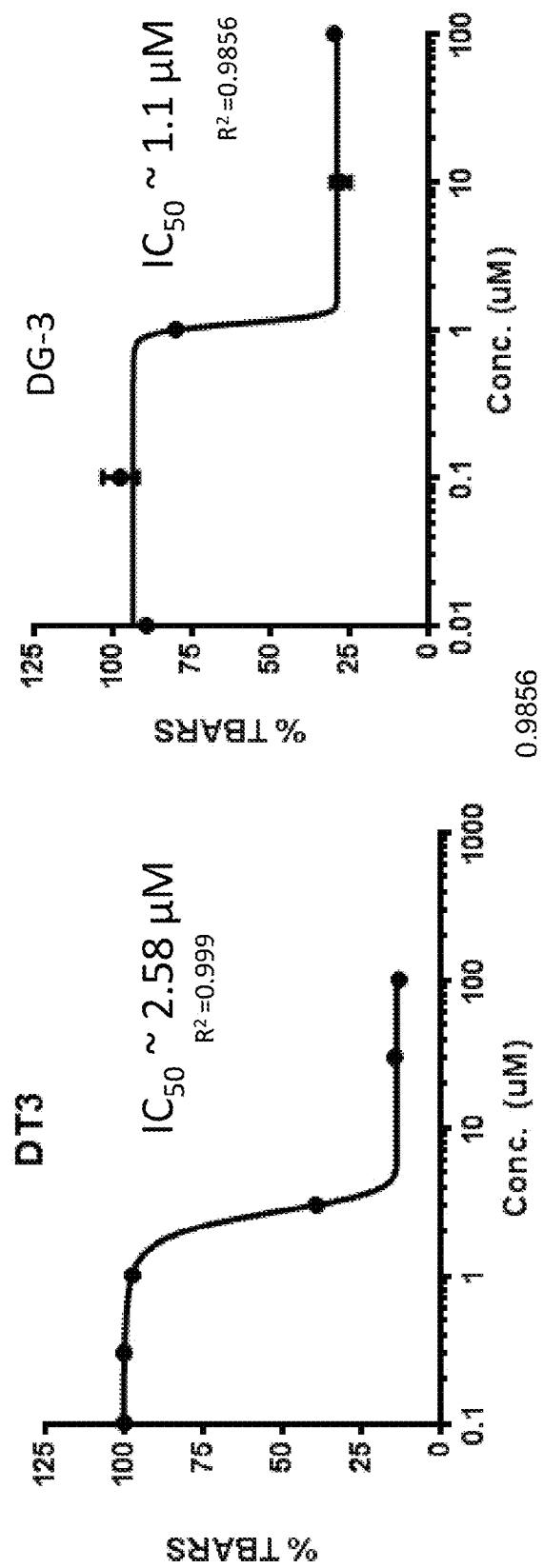
FIG. 4 shows the graphs of the ability of DT3 (δ-tocotrienol) and DG-3 to inhibit TBHP induced lipid peroxidation in Wistar rat liver microsomes. Data are means±SEM of triplicate experiments.

One of the most well-known properties of the vitamin E components is their ability to prevent lipid peroxidation. See Traber et al. (2011) Free Radic Biol Med 51(5):1000-1013. Briefly, the antioxidant activity of DG-3 was evaluated in rat liver microsomes by measuring inhibition of lipid peroxidation after TBHP (thiobarbituric acid reactive substance) treatment. Wistar rat liver microsomes (BD Biosciences) were diluted in phosphate buffer, 0.1 M (pH 7.4), at the final protein concentration of 1 mg/ml. The microsomes were treated with different concentrations of DG-3 or DT3 (diluted with DMSO) and incubated at 37° C. for 1 hour before inducing lipid peroxidation with 200 μM TBHP (DMSO) for 30 min. In the assay for the inhibition of peroxidation of rat liver microsomes treated with 200 μM TBHP, δ-tocotrienol showed an antioxidant potential of $IC_{50}=2.58$ μM, while DG-3 showed a more robust antioxidant potential of $IC_{50}=1.1$ μM (FIG. 4). These results support the notion that DG-3 will have a potent bioactivity when tested in vivo.

Cellular Bioenergetics Measurements

Figure 5:
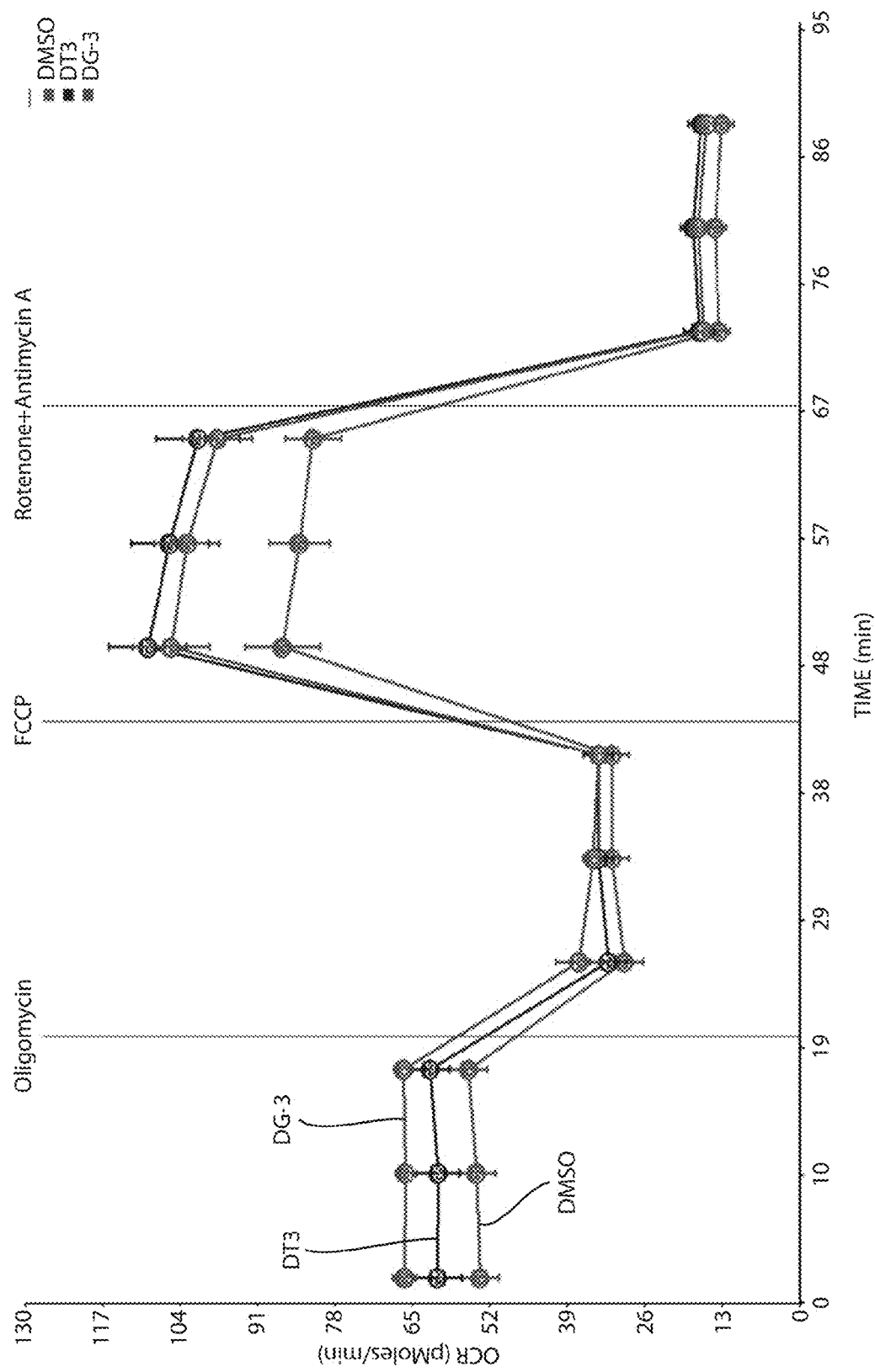
FIG. 5 shows a graph of the effect of DT3 and DG-3 on the oxygen consumption rates (OCR) of cardiomyocytes after the indicated treatments. H9C2 heart cardiomyocytes were treated with 5 μM DT3 or 5 μM DG-3 or vehicle control (DMSO) overnight. Oxygen Consumption Rates (OCR) were measured and cellular bioenergetics profiles were determined using XF96 Seahorse Extracellular Flux Analyzer.
Figure 6:
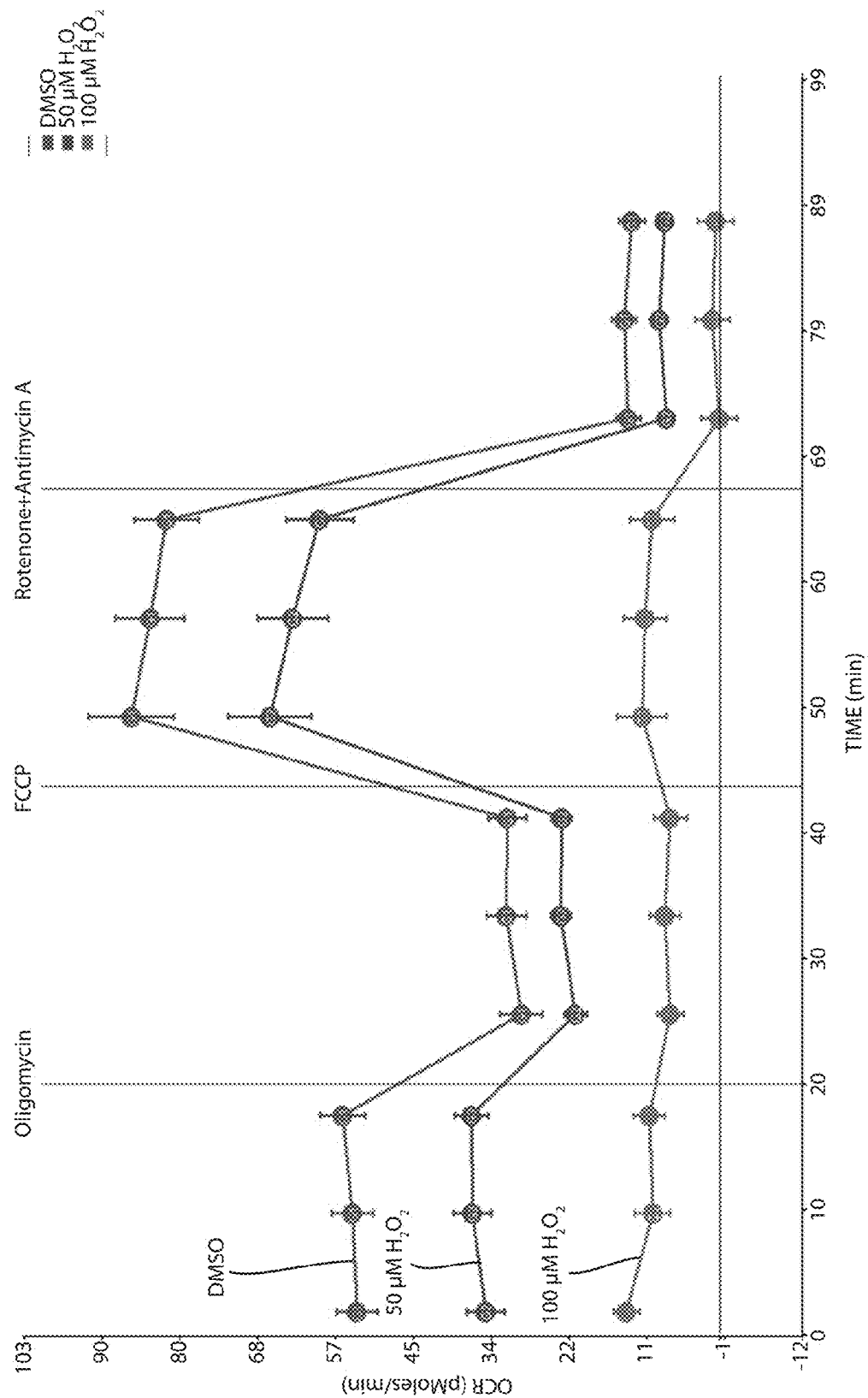
FIG. 6 is a graph showing the effects of hydrogen peroxide on the OCR of cardiomyocytes after the indicated treatments. H9C2 heart cardiomyocytes were exposed to 50 or 100 μM $H_2O_2$ for 4 h. Oxygen Consumption Rates (OCR) were measured and cellular bioenergetics profiles were determined using XF96 Seahorse Extracellular Flux Analyzer.
Figure 7:
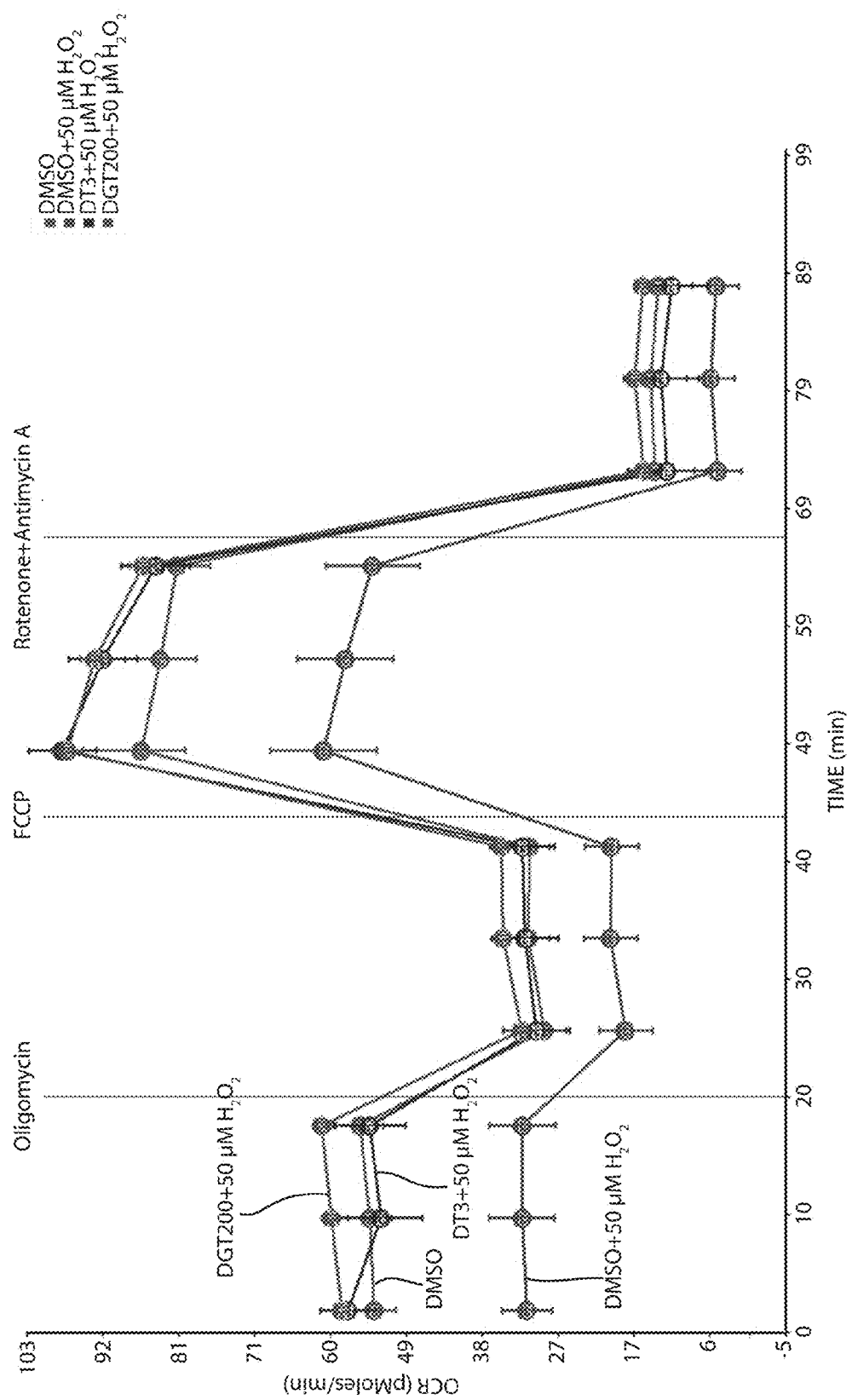
FIG. 7 is a graph showing the effects of 50 μM hydrogen peroxide on the OCR of cardiomyocytes after the indicated pre-treatment with DMSO (dimethylsulfoxide vehicle), DT3 or DG-3. Cellular bioenergetic profiles were determined using XF96 Seahorse Extracellular Flux Analyzer.
Figure 8:
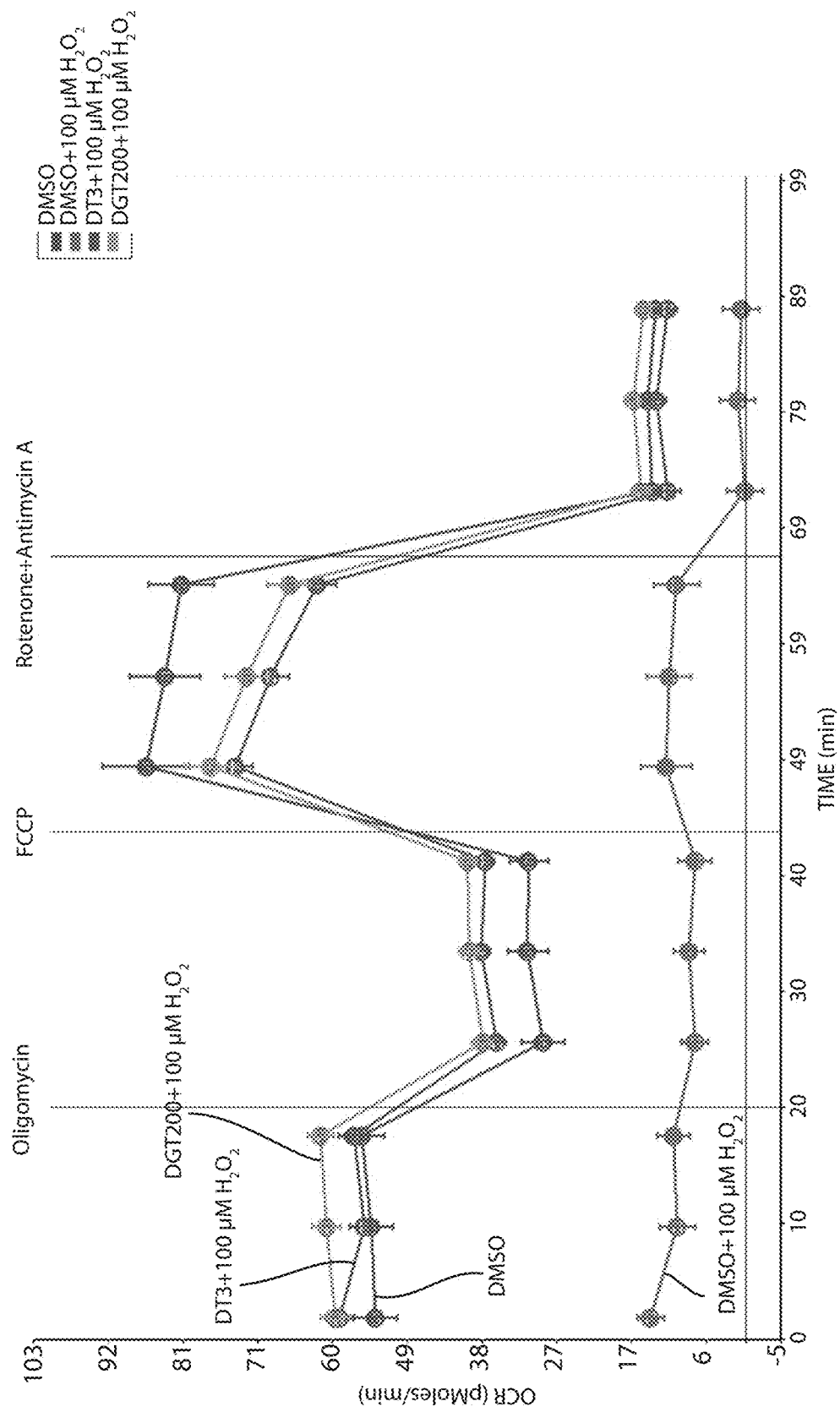
FIG. 8 is a graph showing the effects of 100 μM hydrogen peroxide on the OCR of cardiomyocytes after the indicated pre-treatment with DMSO (dimethylsulfoxide vehicle), DT3 or DG-3. Cellular bioenergetic profiles were determined using XF96 Seahorse Extracellular Flux Analyzer.
Figure 9:
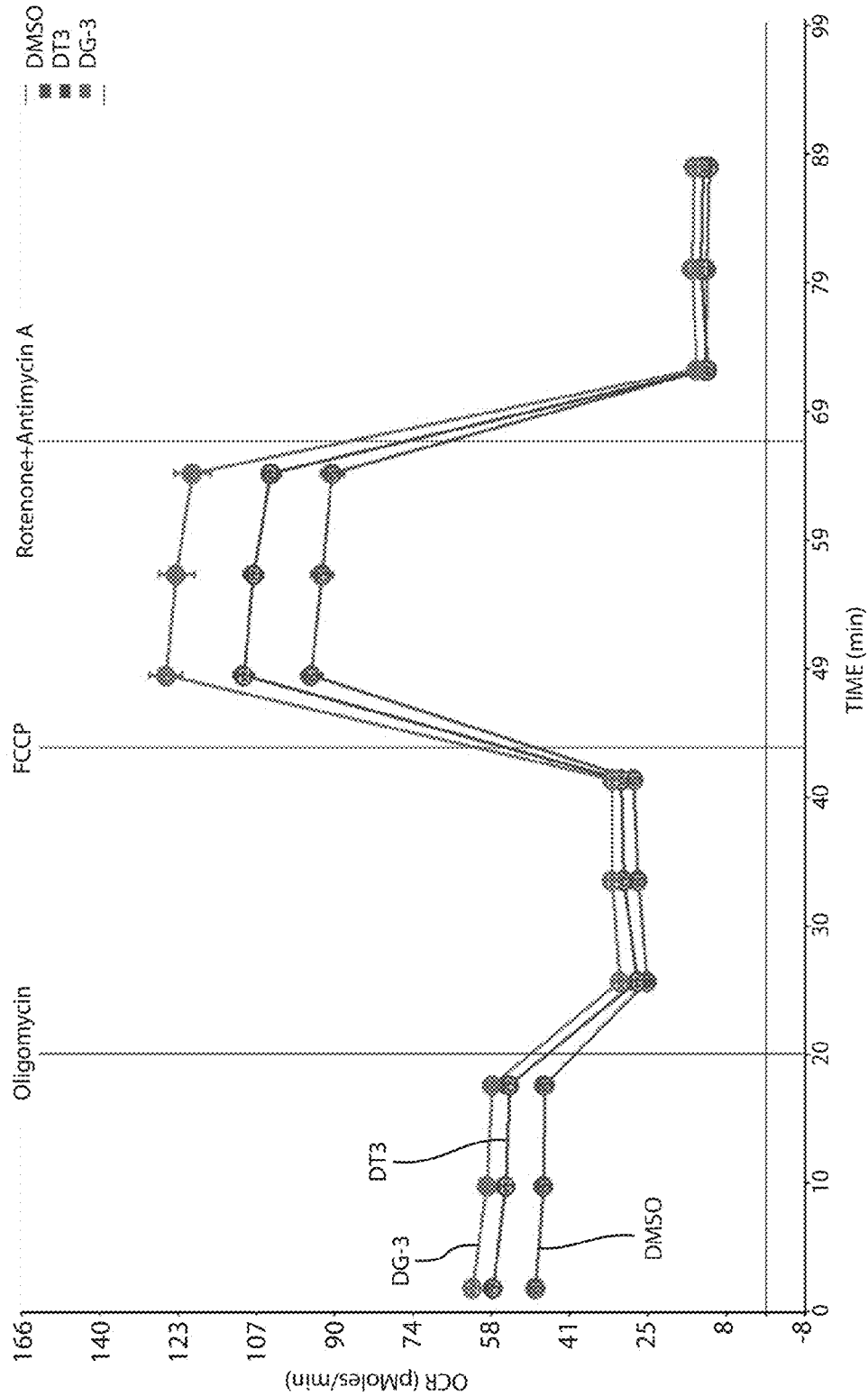
FIG. 9 is a graph showing the effects of 6 Gy ionizing radiation on the OCR of cardiomyocytes after the indicated pre-treatment with DMSO (dimethylsulfoxide vehicle). DT3 or DG-3. Cellular bioenergetic profiles were determined using XF96 Seahorse Extracellular Flux Analyzer 1 h following radiation exposure.

Cellular oxygen consumption rates (OCR) were measured at 37° C. using an XF96 extracellular analyzer (Seahorse Bioscience) as previously described (Ferrick D A, Neilson A, and Beeson C. Advances in measuring cellular bioenergetics using extracellular flux. Drug Discov Today 2008; 13: 268-274). Briefly, 10,000 H9C2 cells per well were plated. The cells were treated with 5 μM DT3 or 5 μM DG-3 or vehicle control (DMSO) overnight. Cells were then exposed to 0, 50 or 100 μM $H_2O_2$ for 4 h or 6 Gy ionizing radiation (IR). The media in the wells were changed to unbuffered Dulbecco's Modified Eagle Medium (DMEM) supplemented with 4 mM glutamate and incubated in a non-$CO_2$ incubator for 1 h at 37° C. Three baseline measurements were acquired before injection of mitochondrial inhibitors or uncouplers. Readings were taken after sequential addition of oligomycin (10 μM), FCCP (10 μM), and rotenone/antimycin A (10 μM). OCR was calculated by the Seahorse XF96 software and represents an average of 12-16 measurements. FIG. 5 shows the effect of treatment with 5 μM DT3 or DG-3 on the Oxygen consumption rates of the cardiomyocytes. DT3 and DG-3 modestly improved the OCR of the cardiomyocytes as compared to controls. FIG. 6 shows the effects on the oxygen consumption rate of the cardiomyocytes of treatment with 50 or 100 μM $H_2O_2$. The 50 μM treatment caused a clear reduction in the OCR of the cells, but the 100 μM treatment reduced the OCR of the cells to almost baseline rates. As shown in FIGS. 7 and 8, respectively pre-treatment of the cells with either DT3 or DG-3 eliminated and significantly reduced the effect of the $H_2O_2$ treatment on the cells. FIG. 9 shows the effects of pretreatment of cells with DT3 or DG-3 to protect the cells from radiation exposure.

Clonogenic Cell Survival Assay

Figure 10:
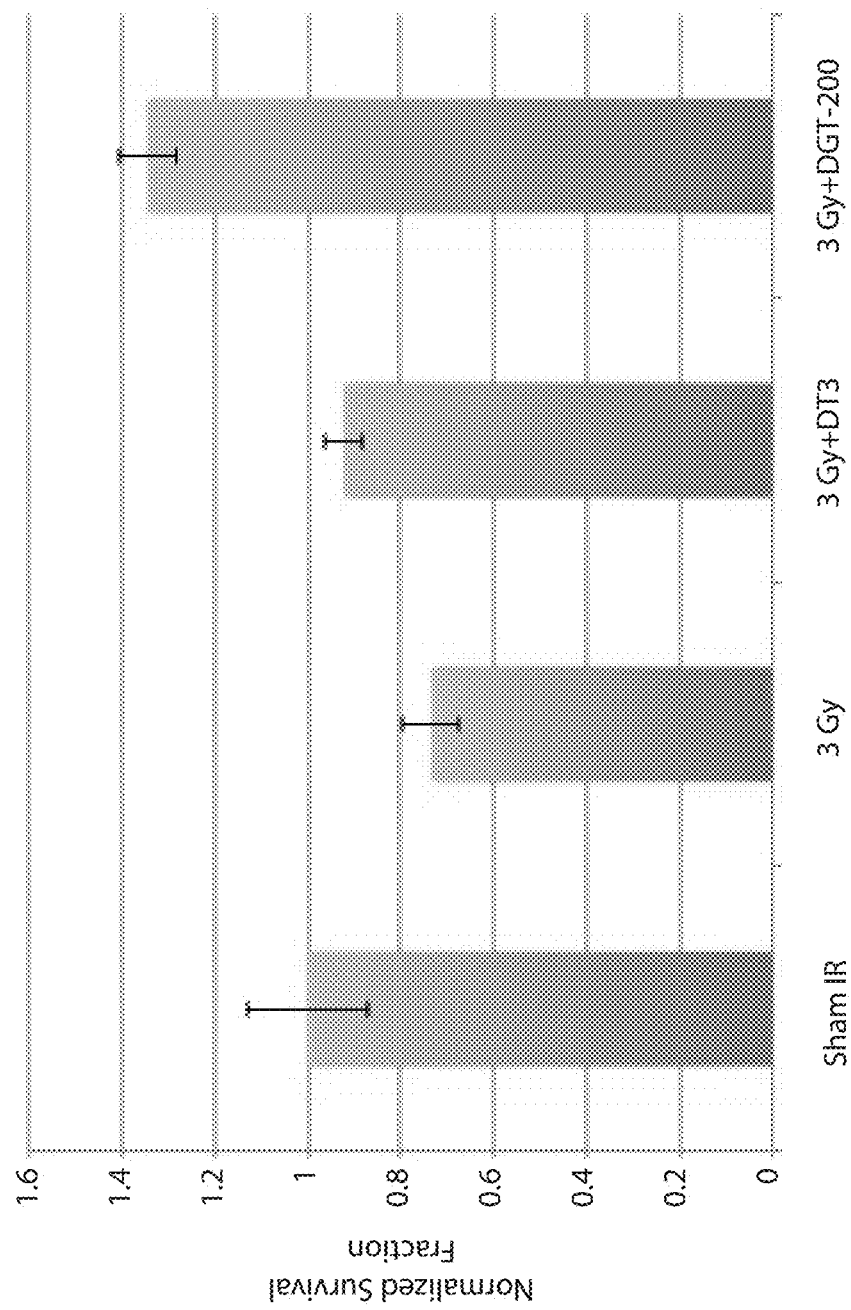
FIG. 10 is a graph showing the normalized survival rates of cardiomyocytes exposed to 3 Gy ionizing radiation after pre-treatment with DMSO, DT3 or DG-3.

Cells were plated in 60-mm dishes with 5 ml of complete medium and allowed to attach and incubate at 37° C. for 24 h. After the cells were irradiated at 3 Gy, they were trypsinized, counted, plated for clonogenic survival as described previously (Aykin-Burns N, Ahmad I M, Zhu Y, Oberley L W, Spitz D R). Increased levels of superoxide and $H_2O_2$ mediate the differential susceptibility of cancer cells versus normal cells to glucose deprivation. (*Biochem J.* 2009; 418:29-37). Proper plating dilutions were determined by experimentation and by the anticipated survival at the dose of ionizing radiation. After 10 days, colonies were fixed with 70% ethyl alcohol, stained with Coomassie blue, and counted. The normalized surviving fraction was determined by dividing the plating efficiency of experimentally manipulated cells by the plating efficiency of sham-treated control cells. The results are presented in FIG. 10 which shows that DG-3 protected the cells from radiation better than DT3.

Radiation Protection Studies

The goal of study was to test the DG-3 composition in the prevailing animal model used to assess the protective effects of potential radiation countermeasures. These experiments use a mouse model of total body irradiation. DG-3 composition was tested for inherent radio-protective activity by subcutaneous administration in the mouse by monitoring treated and untreated mice for 30-day survival after 2 different radiation levels (8.5 Gy and 9.5 Gy). The results of this study showed that the DG-3 composition is an effective radio-protectant in the accepted animal model.

General Experimental Approach:

Male CD2F1 mice at 6-8 weeks of age were housed for 1 week prior to initiating the experiments and permitted food and water ad libitum. Mice were fed vitamin E-deficient chow (Harlan Co.) for one week before the experiment to decrease blood alpha-tocopherol levels, which could interfere with absorption of the radio-protective components of the tested composition. CD2F1 mice show less variation in their response to total body irradiation between different generations than other mouse strains. This mouse model was used to assess the effect of DG-3 composition on radiation injury and lethality, with administration starting 24 hours prior to total body irradiation. This is a typical radioprotection protocol. Table 2 summarizes the experimental procedures.

TABLE 2

Experimental protocol for the radiation protection and toxicity studies

| Subcutaneous injection: | vehicle | vehicle | DG3 composition (300 mg/Kg tocotrienol equivalent) | DG3 composition (300 mg/Kg tocotrienol equivalent) |
|---|---|---|---|---|
| radiation: | yes | no | yes | no |
| # groups: | 1 | 1 | 2 | 1 |
| # mice/group: | 10 | 10 | 10 | 10 |
| # mice: | 10 | 10 | 20 | 10 |

Twenty-four hours before total body irradiation (day −1), mice received, by subcutaneous injection, either vehicle or experimental composition DG-3 standardized to contain 300 mg/Kg tocotrienols (γ and δ). The following day (day 0), mice received total body irradiation, as described below, with a single dose of 8.5 or 9.5 Gy. These dose levels were selected to be near the known LD50 at 30 days (LD50/30) for this mouse strain (8.5 Gy). Thirty-day survival was assessed in these mice. A control (sham) group of mice received DG-3 composition (300 mg/Kg tocotrienol equivalent), but were not subject to irradiation.

Toxicity Screening

In Table 2, two groups of mice received no radiation, one of these received only vehicle and another one received the DG-3 composition (300 mg/Kg tocotrienol equivalent) by subcutaneous injection. A comparison of the thirty-day survival of these two groups using Kaplan-Meier curves showed the absence of toxicity from DG-3 composition.

Procedures:

Total Body Irradiation

Mice received total body irradiation with a single dose, either 8.5 or 9.5 Gy, using a Mark I Model 68A cesium-137 animal irradiator (Shepherd & Associates, San Fernando, Calif.). Un-anesthetized mice were placed in well-ventilated cylindrical chambers divided into 8 "pie slice" compartments by vertical dividers (J. L. Shepherd & Associates), one mouse per chamber, giving the mice ample space to move. The chambers were placed on a turntable rotating at 6 revolutions per minute to assure uniform irradiation. Mice were placed in the irradiator in position #3 and irradiated at a dose rate of 1.09 Gy/min. Hence, the maximum radiation dose required 8.27 minutes of irradiation time; so the mice were in the holders for no more than 10 minutes.

Administration of DG3 Composition

Mice in the experimental group received a subcutaneous injection of 300 mg/Kg of an emulsion of DG3 composition in Tween 80 (5%), PEG 80. On a molar basis, this was equal to 0.756 mmol/Kg. Negative control mice received vehicle only.

Figure 11:
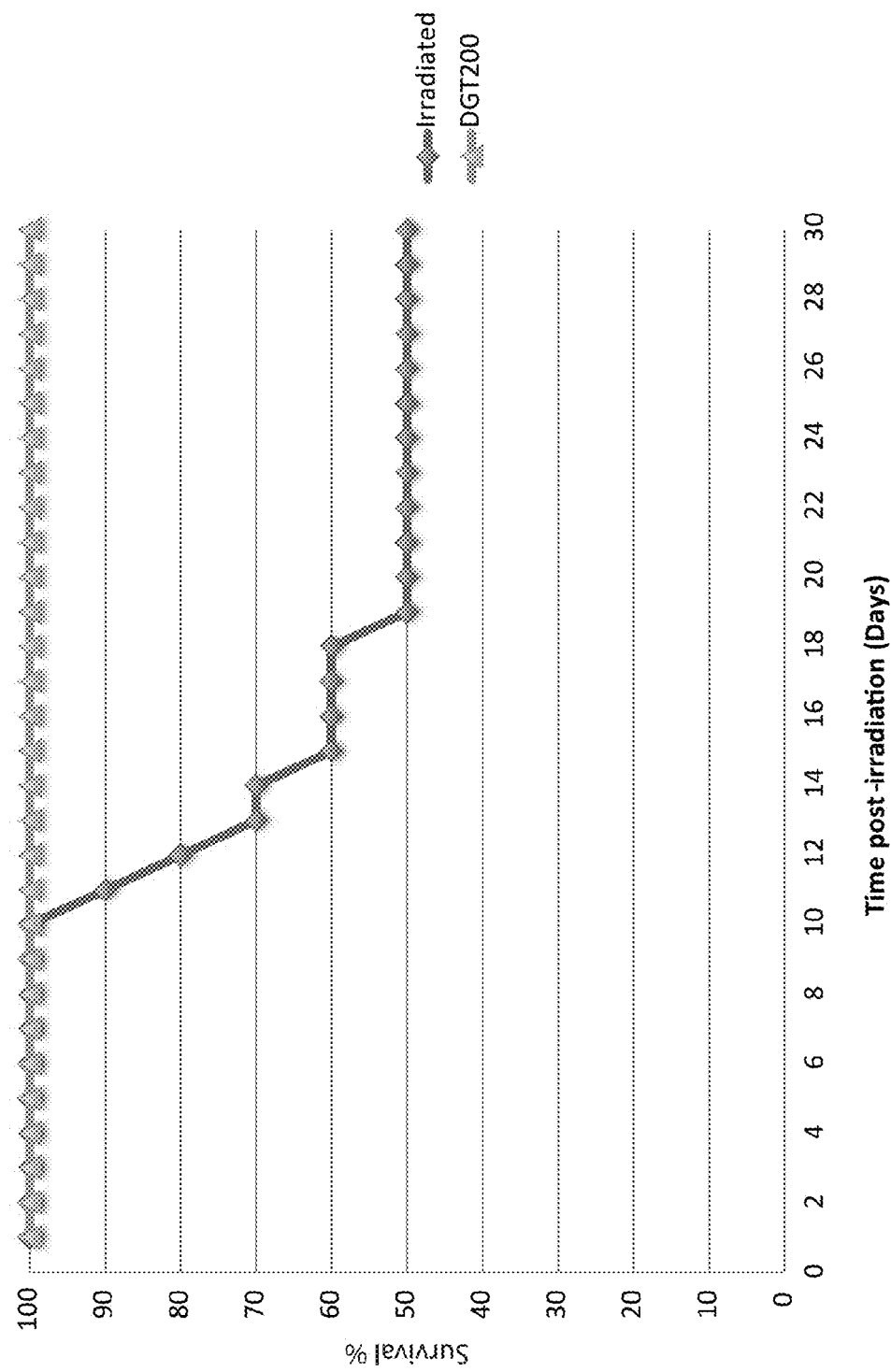
FIG. 11 is a Kaplan-Meier survival curve showing complete (100%) radiation protection of mice exposed to 8.5 Gy of ionizing radiation.
Figure 12:
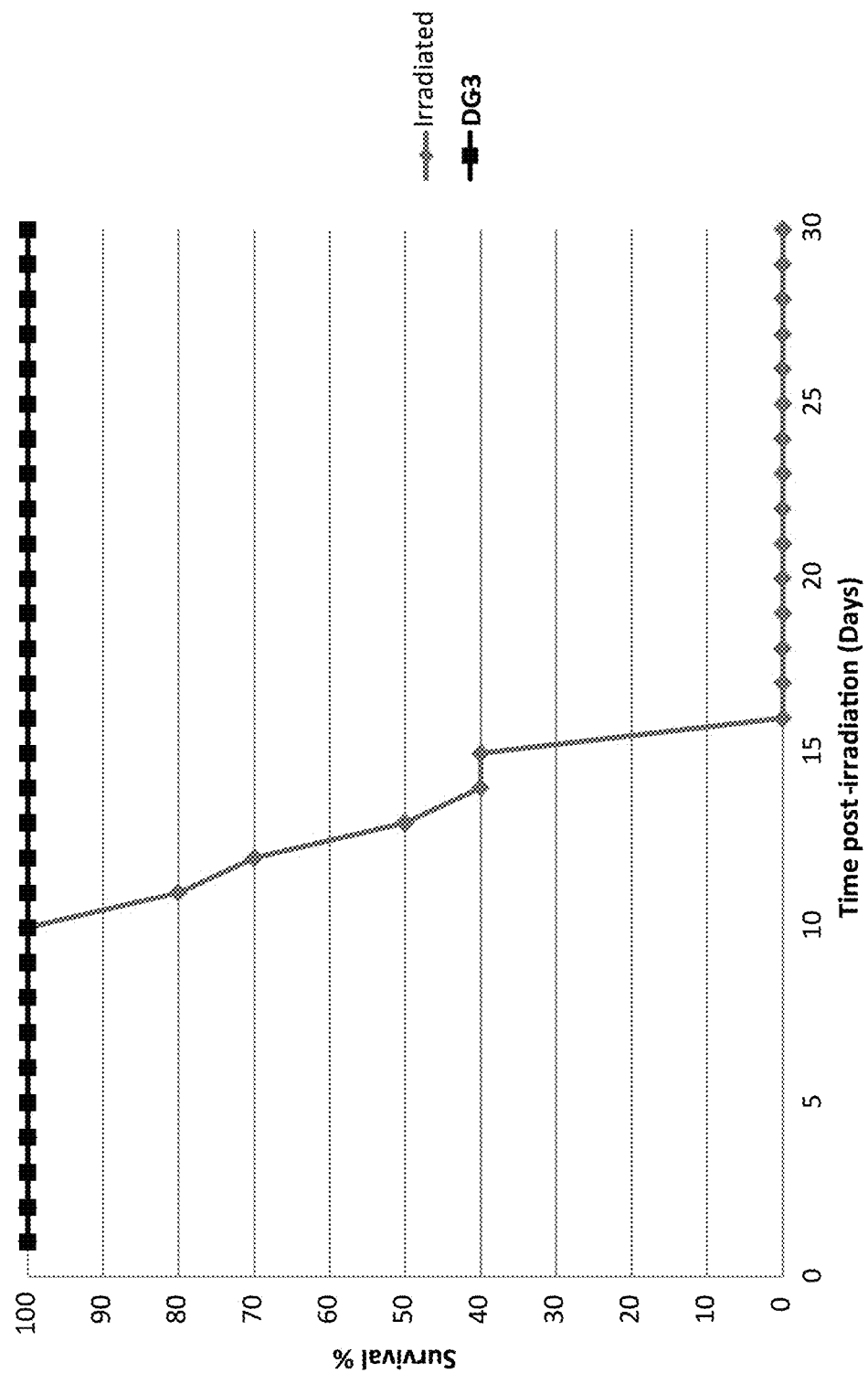
FIG. 12 is a Kaplan-Meier survival curve showing complete (100%) radiation protection of mice exposed to 9.5 Gy of ionizing radiation.

Results:

Results of the experiment, displayed in a Kaplan-Meier curve (FIGS. 11 and 12), show that 100% of mice receiving a single dose of DG-3 composition survived doses of radiation that were 50% (8.5 Gy) and 100% (9.5 Gy) fatal to mice who received vehicle only. Moreover, DG-3 showed no toxic properties of its own. These results constitute conclusive evidence of the radiation protection activity of DG-3 in mice, which has historically been shown to be predictive of radio-protective activity in humans.

We claim:

1. A method of preparing an annatto seed extract having a δ-tocotrienol to γ-tocotrienol ratio of between 7:1 to 9:1, comprising:
    a. Extracting the oil from the annatto seeds to produce annatto seed oil, and
    b. Enriching the tocotrienols from the annatto seed oil via chromatography, wherein the tocotrienols are separated by chromatography using a solvent comprising hexane, wherein the total tocotrienols are between 15% and 95% of the composition and the tocopherols are less than 1% of the extract after the chromatography.

2. The method of claim 1, wherein the oil is hexane extracted from the annatto seeds.

3. The method of claim 1, wherein the tocotrienols are separated by chromatography using a hexane: ethyl acetate solvent or a hexane: isopropanol solvent.

4. The method of claim 3, wherein the hexane: ethyl acetate solvent has a ratio of 90:10.

5. The method of claim 3, wherein the hexane: isopropanol solvent has a ratio of 98:2.

6. A method of treating a subject comprising administering an effective amount of a composition comprising an annatto seed extract having a δ-tocotrienol to γ-tocotrienol ratio of between 7:1 to 9:1 to the subject, wherein the subject is in need of a radioprotectant or for treatment of radiation exposure wherein the total tocotrienols are between 15% and 95% of the composition and the tocopherols are less than 1% of the extract after the chromatography.

7. The method of claim 6, wherein the subject has a condition of radiation exposure.

8. The method of claim 6, wherein the composition is made by a method comprising:
    a. extracting the oil from the annatto seeds to produce annatto seed oil, and
    b. Enriching the tocotrienols from the annatto seed oil via chromatography, wherein the tocotrienols are separated by chromatography using a solvent comprising hexane.

9. The method of claim 6, wherein the tocotrienols are more than 50% of the composition.

10. The method of claim 6, wherein the composition is substantially free of tocopherols.

11. The method of claim 6, wherein the composition comprises at least 100 mg/mL total tocotrienol.

12. The method of claim 6, wherein the composition comprises at least 500 mg/mL total tocotrienol.

13. The method of claim 6, wherein the composition is a pharmaceutical composition further comprising a pharmaceutically acceptable carrier.

14. The method of claim 12, wherein the pharmaceutical composition comprises at least 1 g total tocotrienols in a dosage form.

15. The method of claim 1, wherein the tocotrienols are more than 50% of the composition.

16. The method of claim 1, wherein the composition is substantially free of tocopherols.

17. The method of claim 1, wherein the composition comprises at least 100 mg/mL total tocotrienol.

18. The method of claim 1, wherein the composition comprises at least 500 mg/mL total tocotrienol.

* * * * *

UNITED STATES PATENT AND TRADEMARK OFFICE
CERTIFICATE OF CORRECTION

PATENT NO. : 9,993,456 B2
APPLICATION NO. : 15/021376
DATED : June 12, 2018
INVENTOR(S) : Cesar M. Compadre et al.

Page 1 of 1

It is certified that error appears in the above-identified patent and that said Letters Patent is hereby corrected as shown below:

On the Title Page

Item (73), add the following Assignee:
BioVentures, LLC
4301 W. Markham Street
831
Little Rock, AR 72205-7199

The following Assignee is to be removed:
The Board of Trustees of the University of Arkansas
Little Rock, AR Signed and Sealed this
Twenty-fourth Day of September, 2019

Andrei Iancu
*Director of the United States Patent and Trademark Office*